United States Patent [19]
Bartlett

[11] Patent Number: 6,155,999
[45] Date of Patent: Dec. 5, 2000

[54] TENDON DECOMPRESSION DEVICE

[76] Inventor: Margaret D. Bartlett, 28273 Tampico Rd., Corvallis, Oreg. 97330

[21] Appl. No.: 09/320,173

[22] Filed: May 26, 1999

[51] Int. Cl.[7] ..................................................... A61F 13/00
[52] U.S. Cl. ................................ 602/60; 602/41; 602/53; 602/54; 602/61
[58] Field of Search ....................... 602/41–59; 606/213, 606/214, 215, 216; 128/888, 889

[56] References Cited

U.S. PATENT DOCUMENTS 679,993  8/1901  Ross et al. ............................... 606/215

OTHER PUBLICATIONS

Merck Manual, 1987: pp. 1269–1270.
Sammons Preston, 1998 (Catalog), p. 354.
MDC Meyer Distributing Co., 1999 (Catalog), pp. 96–97.

Primary Examiner—Kim M. Lee
Attorney, Agent, or Firm—Robert E. Howard

[57] ABSTRACT

A tendon decompression device for alleviating tendinitis pains, such as tennis elbow. The device is comprised of an adhesive tape base strip which can be adhered to the skin. The base strip has a buckle subassembly at one end and a tensioning strap subassembly at the other end. A tensioning strap passes through an opening in the buckle, permitting the buckle subassembly to be pulled towards the tensioning strap subassembly. Locking means are provided for locking the tensioning strap in place once sufficient tension has been achieved.

7 Claims, 2 Drawing Sheets

TENDON DECOMPRESSION DEVICE

BACKGROUND OF THE INVENTION

This invention relates to a tendon decompression device useful in alleviating the pains associated with tendinitis, particularly that associated with "tennis elbow" and similar syndromes.

Tennis elbow is a strain of the lateral forearm muscles or their tendinous attachments near their origin on the lateral epicondyle of the humerus. "Golfer's elbow" is a comparable syndrome involving forearm pronators and their attachments.

According to the Merck Manual (15th edition, 1987, pages 1269 and 1270), treatment for alleviating the symptoms of tennis elbow involves wrapping a four inch strap tightly around the forearm, the strap being worn just distal to the elbow. Other devices similarly involve applying pressure to the forearm with various straps and bands wrapped around the forearm. Likewise, devices available for tendinitis at the knee involve straps applied circumferentially around the fibia.

SUMMARY OF THE INVENTION

An object of the present invention is to provide a simple disposable device for alleviating the symptoms of tennis elbow and similar syndromes affecting major joints.

The device of the present invention is comprised of an adhesive strip having a buckle subassembly located at a first end and a tensioning strap subassembly located at the second end.

The adhesive strip of the device is applied to the skin over the location of the affected tendon of the involved limb, such as a forearm. The adhesive strip is applied with its longitudinal axis perpendicular to the longitudinal axis of the limb. The tensioning strap subassembly passes through the buckle subassembly and when tightened draws the two ends of the adhesive strip toward each other thereby drawing the skin to which the two ends are adhered toward each other which decompresses the adjacent underlying muscle or tendon strictures.

DESCRIPTION OF PREFERRED EMBODIMENTS

Figure 1:
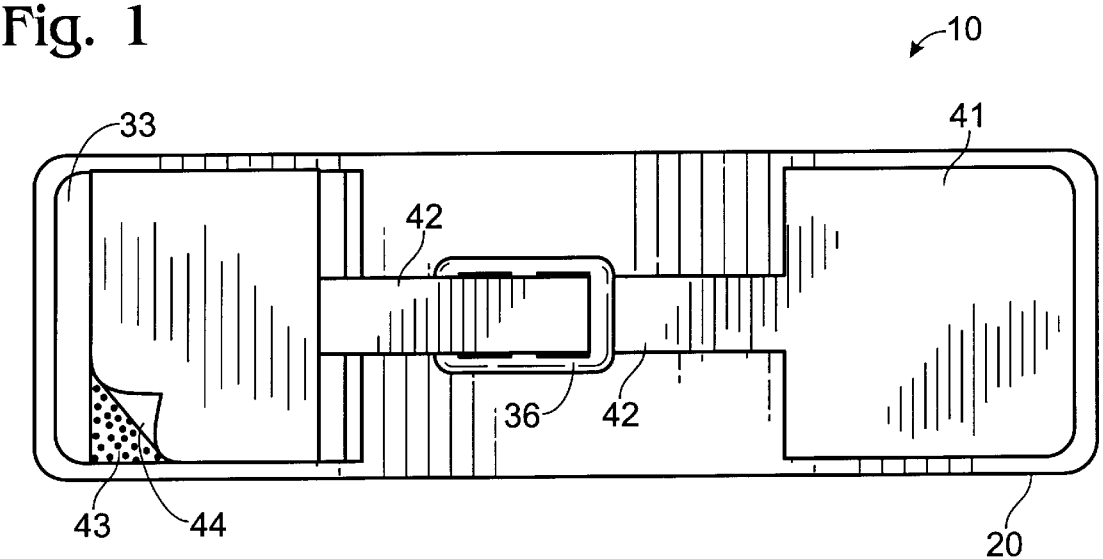
FIG. 1 is a top view of the device of the invention shown in its untensioned state.

In FIG. 1 the top of tendon decompression device 10 of the invention is shown in its untensioned state, i.e., as it appears before application to the affected limb of a patient.

Device 10 is comprised of an adhesive tape base strip 20 having a buckle subassembly 30 and a tensioning strap subassembly 40, both being attached to the upper, non-adhesive surface 22 of adhesive tape base strip 20.

Figure 5:
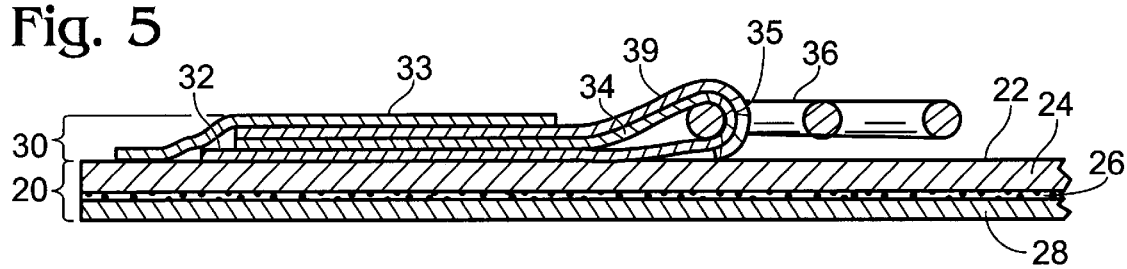
FIG. 5 is a side sectional view taken along line 5—5 of FIG. 2.

Adhesive tape base strip 20 is shown in cross-section in FIG. 5, and is comprised of a moisture vapor permeable substrate 24 having an adhesive layer 26 suitable for attaching to the skin of a human being, and a non-adhesive, peelable sheet 28 temporarily adhered to adhesive layer 26.

Although many commercially available adhesive tapes may be used for base strip 20, the tape should have sufficient strength characteristics to allow for its use in the invention described herein. A suitable tape for use as base strip 20 is that sold by Smith and Nephew Associated Companies p.l.c. under the trademark "Hypafix".

Figure 2:
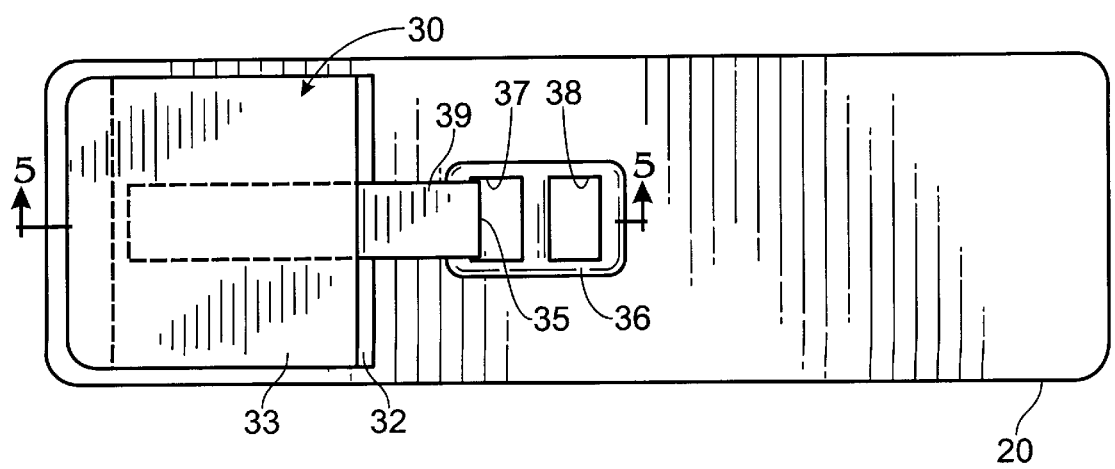
FIG. 2 is a top view of the buckle subassembly of the device of the invention.

The buckle subassembly 30 is shown in top view in FIG. 2 and in a side, cross-sectional view in FIG. 5. Buckle 30 is comprised of a lower tape member 32, an upper tape member 33, and a tab 34 folded back to form a loop 35 to which is secured buckle member 36.

Lower tape member 32 has an upper, non-adhesive surface and a lower, adhesive surface adhered to the upper surface 22 of base strip 20.

Tab 34 is preferably formed integral with lower tape member 32 and, since the lower surface of lower tape member 32 is adhesive, when it is folded back to form loop 35 it is covered with a non-adhesive layer 39 to effect a non-adhesive upper layer for at least the exposed portion of tab 34. Non-adhesive layer 39 can either be a separate piece of non-adhesive material such as cloth, paper, or film, or when tab 34 is cut from tape 32 (in the preferred embodiment) it can be formed twice as wide as desired for the final tab width, and folded back on itself to thereby present a non-adhesive exposed surface.

Upper tape member 33 secures folded back tab 34 to lower tape member 32 to thereby form a strong loop 35. Buckle 36 has two openings, 37 and 38. Buckle 36 is held by loop 35 by virtue of tab 34 being passed through opening 37 prior to its being folded back and secured by upper tape member 33.

Many commercially available adhesive tapes may be used to form the various components of buckle subassembly 30. A rigid strapping tape sold by Donjoy/Smith and Nephews has been found to be satisfactory.

Tensioning strap subassembly 40 is comprised of a fixed base 41, a strap member 42 extending from fixed base 41 (and preferably formed integral therewith), and an anchor member 43. The upper surfaces of base 41 and strap 42 are non-adhesive with the lower surfaces thereof being adhesive. The adhesive lower surface of base 41 is adhered to the non-adhesive upper surface 22 of adhesive tape base strip 20. The adhesive lower surface of strap 42 is either covered with a non-adhesive material, or (preferably) when cut from a larger piece of adhesive tape to form subassembly 40, is cut twice as wide as the desired final width for strap 42 and folded back on itself to thereby render its lower surface non-adhesive.

An intermediate portion of strap 42 passes through opening 38 in buckle 36, and strap 42 is secured at its outer end to anchor member 43.

Figure 3:
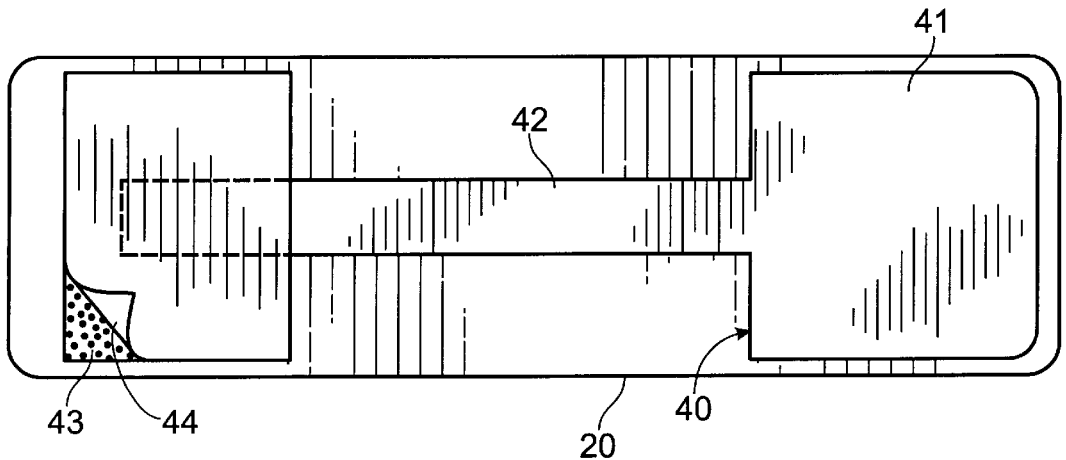
FIG. 3 is a top view of the tensioning strap subassembly of the device of the invention.
Figure 4:
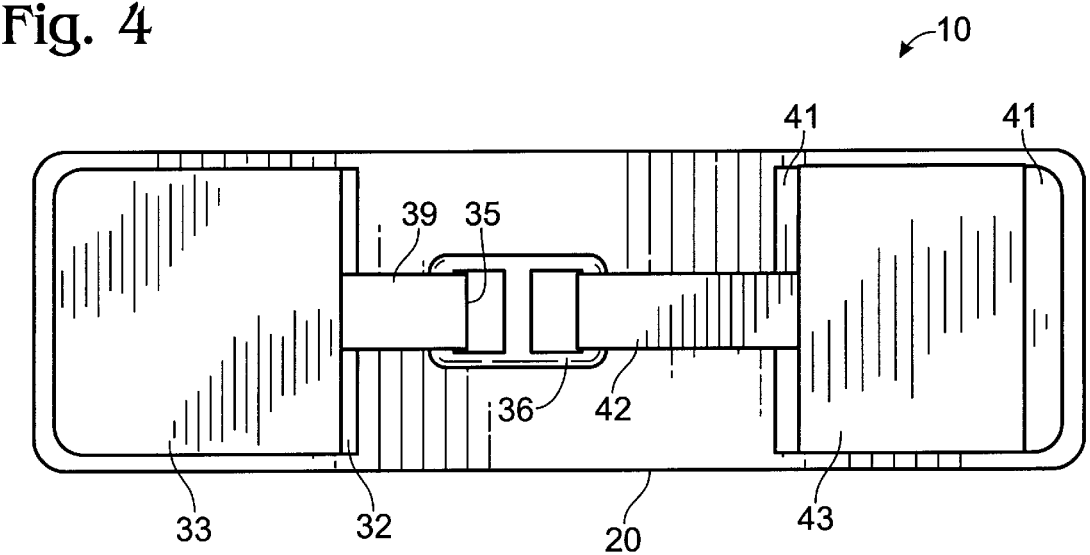
FIG. 4 is a top view of the device of the invention shown in its tensioned state.

In the preferred embodiment, anchor member 43 is formed of a rectangular piece of adhesive tape with the upper surface of anchor member 43 (as viewed in FIG. 3) being adhesive. The adhesive upper surface of anchor member 43 is attached to the underside of the outer end of strap 42, as shown. A non-adhesive, peelable sheet 44 is temporarily adhered to and covers the remainder of the upper adhesive surface of anchor member 43.

Alternatively, anchor member 43 could be formed integral with strap 42.

Many commercially available adhesive tapes may be used to form tensioning strap subassembly 40, including the Smith and Nephew tape suggested above for use with buckle subassembly 30.

In use, the tendon decompression device of the invention is applied to the affected limb (such as to the forearm just below the elbow in the case of tennis elbow) by removing peelable sheet 28 and adhering substrate 24 to the skin with the longitudinal axis of device 10 perpendicular to the longitudinal axis of the affected limb.

Anchor member 43, and the outer end of tensioning strap 42 attached thereto, is then pulled up and back across buckle 36 towards fixed base 41. As anchor member 43 is pulled toward fixed base 41 that portion of tensioning strap 42 in contact with buckle 36 pulls against it, and buckle subassembly 30 (and that portion of substrate 24 underlying buckle subassembly 30) is pulled towards fixed base 41, and vice versa.

Either at the beginning of such tensioning or thereafter, peelable sheet 44 is removed, thereby exposing the adhesive surface of anchor member 43, which said adhesive surface, although originally facing upwards, is now facing downwards toward fixed base 41. Upon satisfactory tension being achieved, the adhesive surface of anchor member 43 is contacted with the upper, non-adhesive surface of fixed base 41 and pressed downwards to effect good adhesion therebetween, thereby locking in place the relative positions of buckle subassembly 30 and tensioning strap subassembly 40.

Although adhesive tape is the preferred manner of attaching anchor member 43 to fixed base 41, other attachment means could be used, such as hook and loop ("Velcro") fasteners.

What is claimed is:

1. A tendon decompression device comprising:

an adhesive tape base strip comprised of a moisture vapor permeable substrate having first and second ends, a mid-section, and upper and lower surfaces, said lower surface having an adhesive layer located thereon;

a buckle subassembly attached to said upper surface of said base strip adjacent its first end, said buckle subassembly including at least one tape member adhesively attached to the upper surface of said base strip, said tape member having a loop extending therefrom toward the midsection of said base strip, said buckle subassembly also including a buckle member having first and second openings therein, said loop passing through said first opening in said buckle member to thereby hold said buckle member in place;

a tensioning strap subassembly attached to said upper surface of said base strip adjacent its second end, said tensioning strap subassembly including a fixed base having an upper and lower surface, said fixed base being adhesively attached at its lower surface to the upper surface of said base strip, said fixed base having a strap member extending therefrom toward the mid-section of said base strip, said strap member passing through said second opening in said buckle member and terminating in an outer end, said outer end of said strap member having an anchor member attached thereto, said strap member having a length sufficient to enable said anchor member to be placed into contact with the upper surface of said fixed base when said strap member is folded back on itself at said buckle and said anchor member pulled toward said fixed base under tension; and means for attaching said anchor member to said fixed base when brought into contact therewith.

2. The device of claim 1 wherein said means for attaching said anchor member to said fixed base is an adhesive.

3. The device of claim 2 wherein said adhesive is located on the surface of said anchor member which is to be placed into contact with the upper surface of said fixed base.

4. The device of claim 3 wherein the adhesive surface of said anchor member is covered with a non-adhesive, peelable sheet.

5. The device of claim 1 wherein said buckle subassembly is comprised of a lower tape member, an upper tape member, and a tab extending from and integral with said lower tape member, said tab being folded back and secured between said lower and upper tape members to thereby form said loop.

6. The device of claim 1 wherein said strap member of said tensioning strap subassembly is integral with said fixed base.

7. The device of claim 1 wherein said adhesive lower surface of said adhesive tape base strip has a non-adhesive, peelable sheet adhered to said adhesive layer on said lower surface.

* * * * *